United States Patent [19]

Simonson

[11] Patent Number: 5,665,559
[45] Date of Patent: Sep. 9, 1997

[54] PRODUCTION OF MONOCLONAL ANTIBODIES TO BACTEROIDES GINGIVALIS BY HYBRIDOMA BGII, VF9/2D

[75] Inventor: Lloyd G. Simonson, Deerfield, Ill.

[73] Assignee: The United States of America as represented by the Secretary of the Navy, Washington, D.C.

[21] Appl. No.: 356,899

[22] Filed: May 18, 1989

[51] Int. Cl.$^6$ .................. G01N 33/569; G01N 33/577; C07K 16/12
[52] U.S. Cl. .................. 435/7.32; 435/7.5; 530/388.2; 530/391.3
[58] Field of Search .................. 530/387, 388.2, 530/391.3; 435/240.27, 172.2, 7.32, 7.5; 436/548

[56] References Cited

U.S. PATENT DOCUMENTS 4,689,221  8/1987  Kiyoshige et al. .................. 424/87

OTHER PUBLICATIONS

Stedman's Medical Dictionary, 24th Edition, Williams and Wilkins, Baltimore, 1988, p. 620.
Miyoshi et al., Infection and Immunity 53(2): 366–371, 1986.
Hanazawa et al., Infection and Immunity 46(1): 258–287, 1984.
Naito et al., Infection and Immunity 50(1): 231–235, 1985.
Chen et al., Infection and Immunity 54(3):798–803, 1986.
Tijssen, *Practice and Theory of Enzyme Immuno assays*, Elsevier, Amsterdam, 1985. pp. 1–7.
Simonson et al., J. Dent Res., 65(2), pp. 95–97, Feb., 1986.

*Primary Examiner*—Marian C. Knode
*Assistant Examiner*—Donna C. Wortman
*Attorney, Agent, or Firm*—A. D. Spevack, Esq.; William Garvert, Esq.

[57] ABSTRACT

A monoclonal antibody is disclosed which is reactive to *Bacteroides gingivalis* and produced by the hybridoma deposited under ATCC HB 9968. The invention also discloses diagnostic reagents and methods for detecting *Bacteroides gingivalis* utilizing the hybridoma deposited under ATCC HB 9968.

17 Claims, No Drawings

PRODUCTION OF MONOCLONAL ANTIBODIES TO BACTEROIDES GINGIVALIS BY HYBRIDOMA BGII, VF9/2D

STATEMENT OF GOVERNMENT INTEREST

The invention described herein may be manufactured and used by or for the Government of the United States of America for Governmental purposes without the payment of any royalties thereon or therefor.

BACKGROUND OF THE INVENTION

1. Field of the Invention

This invention relates to monoclonal antibodies produced by hybridoma cell lines created by the fusion of myeloma cell lines with lymphocytes.

The invention further relates to methods for detecting anaerobic microorganisms in clinical samples; more specifically the present invention relates to methods for detecting Bacteroides species, common etiological agents in human anaerobic infections (Gorbach and Bartlett, *New England Journal of Medicine*, 290, 1177, 1237, 1289 (1974)).

It has now been found that the fusion of a mouse myeloma cell line, X63-Ag8.653, with a BALB/c mouse lymphocyte creates a hybridoma which produces a monoclonal antibody which is capable of specifically detecting 14 strains of *Bacteroides gingivalis*.

2. Discussion of the Prior Art

The black-pigmented oral anaerobe *Bacteroides gingivalis* has been increasingly implicated as an etiologic agent of severe periodontitis in adults (Slots, *Journal of Dental Research*, 63, 412 (1984)). Therefore, the detection of this anaerobic micro-organism in a clinical sample may serve as an important diagnostic indicator. Because of the difficulty and amount of time needed to culture, isolate and identify *B. gingivalis* from clinical specimens, serological methods would greatly aid in its detection. Before the use of hybridoma to produce monoclonal antibodies, species specific antibodies were made by adsorbing polyclonal animal sera with cross-reacting antigens. The use of an enzyme linked immunosorbent assay as a rapid serological method of identifying oral species of Bacteroides is described by Ebersole, et al., *Journal of Clinical Microbiology*, 19, 639 (1984). However, antisera prepared in animals are heterogeneous, unpredictable, and very limited in supply. The advent of a classical technique to produce monoclonal antibodies (Kohler and Milstein, *Nature*, 256, 495 (1975)) has allowed for the generation of immunodiagnostic reagents which are highly specific, homogeneous, and unlimited in supply.

A simplified technique based on the Kohler and Milstein methodology for creating hybridomas that produce monoclonal antibodies was described by Fazekas de St. Groth and Scheidegger (*Journal of Immunological Methods*, 35, 1 (1980)). The conditions described by Fazekas de St. Groth and Scheidegger have been utilized frequently; these conditions were modified to obtain the hybridoma producing the monoclonal antibody of the present invention (Simonson, et al., *Journal of Dental Research*, 65, 95 (1986)).

Recently, Strosberg, et al. disclosed in U.S. Pat. No. 4,780,407 a process for the immunological determination of *Legionella pneumophilia* bacteria using a monoclonal antibody produced by a hybridoma cell-line.

SUMMARY OF THE INVENTION

It has been found that the fusion of a mouse myeloma cell line with a mouse lymphocyte creates a hybridoma cell line which produces a uniquely active monoclonal antibody. This antibody is uniquely specific for the bacterial epitope associated with the species *Bacteroides gingivalis*.

The uniquely active monoclonal antibody of the present invention may be included in diagnostic reagents and methods used to detect the oral anaerobe *Bacteroides gingivalis*.

DESCRIPTION OF THE PREFERRED EMBODIMENT

It has been found that, as noted above, the fusion of a mouse myeloma cell line with a mouse lymphocyte creates a hybridoma which produces a uniquely active monoclonal antibody. This hybridoma has been deposited under the terms of the Budapest treaty on the international recognition of the deposit of microorganisms for the purposes of patent procedure on Jan. 12, 1989, with the American Type Culture Collection, 12301 Parklawn Drive, Rockville, Md. 20852, USA under accession number ATCC HB 9968.

The hybridoma techniques used in this investigation were similar to those first reported by Kohler and Milstein, ibid., and as modified by de St. Groth and Scheidegger, ibid., the basic fusion protocol followed utilized Iscove's basal medium.

The unique antibody produced by the hybridoma may be linked directly or indirectly to a detectable labeling group. Indirect linkage to a detectable label may be achieved using avidin-biotin technology.

Detectable labels that may be employed in the present invention include enzymes, fluorescent labels and radionuclides. The preferred label is an enzyme that binds to the antibody at a position which does not interfere with the binding of the antibody to the antigen.

Thus, the enzyme should possess potentially reactive groups to which the antibody can be coupled without destroying enzyme activity and the enzyme should not occur naturally to an appreciable extent in the type of tissue to be assayed for the said biological substance. In addition, the enzyme should have a relatively long shelf life, a high specific activity and also be capable of being easily assayed, for example, with a visible light spectrophotometer.

Examples of enzymes which may conveniently be employed in the present invention are: maleate dehydrogenase, staphylococcal nuclease, δ-5-ketosteroid isomerase, yeast alcohol dehydrogenase, yeast glucose-6-phosphate dehydrogenase, α-glycerophosphate dehydrogenase, triose phosphate isomerase, horseradish peroxidase, alkaline phosphatase, asparaginase, glucose oxidase, beta-galactosidase, ribonuclease and urease. Normally, it is preferred to purify the enzyme, for example, by dialysis against saline, before use.

A radionuclide such as $^{125}I$ or $^{32}P$ may also be used as the label.

The preparation of the enzyme-labelled antibody for use in the present invention can take place via conventional methods known in the art.

Examples of the coupling of biological substances to enzymes are described in, for example, L. A. Steinberger, Immunocytochemistry, Prentice Hall, New Jersey (1974).

As pointed out above, indirect linkage of antibodies to detectable labels may be accomplished with avidin-biotin technology. The use of primary-secondary antibody techniques in tandem with avidin-biotin technology affords an assay with increased sensitivity. A review of the avidin-biotin technology appears in *Analytical Biochemistry*, 171, 1 (1988).

The invention is illustrated further by the following examples which are not to be construed as limiting the invention in scope or spirit to the specific procedures described in them.

EXAMPLE I

Production of Monoclonal Antibody Specific for *Bacteroides Gingivalis*

1. Preparation of Antigens

*Bacteroides gingivalis* ATCC 33277 was routinely grown in Wilkins-Chalgren broth supplemented with hemin, 5 µg/mL, and menadione, 0.3 µg/mL. Blood agar plates were prepared by supplementing the broth with 5% (v/v) defibrinated laked horse blood and 1.5% agar. Both soluble and fixed whole-cell antigens were prepared from cells grown in an anaerobic chamber containing 80% nitrogen, 10% carbon dioxide, and 10% hydrogen, at 37° C. for from 48 to 72 hours. The cells were washed three times with 0.01 mol/L phosphate—0.15 mol/L NaCl pH 7.2 buffer (PBS). Whole-cell antigens were fixed overnight in 0.6% formalin-PBS, washed with PBS, and re-suspended in sterile 0.015 mol/L NaCl at a concentration of 10 mg (wet weight) per mL.

2. Immunization

Male and female eight-to-ten-week-old BALB/c BYJ mice were challenged with 0.05 mL soluble antigen per rear foot pad, after the antigen had been mixed 1:1 (v/v) with Freund's complete adjuvant. Each animal was also initially injected intraperitoneally with 0.1 mL of the formalinized whole-cell antigen preparation (1 mg). Marginal tail vein booster injections were given 15 days later, using 0.1 mL (1 mg) of PBS washed whole-cell antigen. A final intravenous booster of the whole-cell immunogen was always given three days prior to the hybridoma fusion.

3. Hybridoma Fusion

The X63-Ag8.653 mouse myeloma cell line was used for hybridoma fusions. Kearney, et al., *Journal of Immunology*, 123, 1548 (1979), demonstrated that this cell line had lost the ability to express its own immunoglobulins. The myeloma cells were grown to log phase and fused with donor splenocytes using pre-screened (polyethylene glycol) PEG 4000 (50% in serum-free basal medium). The cell mixture was pelleted and treated for one minute with the PEG mixture, diluted with 20 mL of culture medium containing 20% fetal bovine serum (FBS), and re-centrifuged at 200 g for five minutes. The pellet was re-suspended in Dulbecco's Modified Eagle Medium (DMEM) with 20% FBS and 2×HAT (culture medium containing hypoxanthine, aminopterin, and thymidine) and dispensed in 50 µL aliquots per well to 96-well plates. One day prior to fusion, the 96-well culture plates were seeded with $1 \times 10^5$ BALB/c splenocyte feeder cells per well in 50 µL of basal medium. Hybridomas were grown at 37° C., with humidity from 70 to 80% and carbon dioxide from 6 to 8%. Well supernatants from the initial plating were assayed by the enzyme linked immunosorbent assay (Ebersole et al., *Journal of Clinical Microbiology*, 19, 639 (1984)) (ELISA) for antibody to the appropriate Bacteroides antigen preparation, as described below. Positive wells were recloned first by limiting dilution and second by soft-agar cloning. Unlike previous studies, these cloning procedures involved using splenocytes from rice rats (*Oryzomys palustris*) for feeder cells instead of the more expensive BALB/c-derived feeder cells. The use of both cloning techniques was thought to increase the likelihood of monoclonality.

The hybridoma fusion resulted in somatic cell hybridomas which secreted monoclonal antibodies to epitopes of *Bacteroides gingivalis*. The protocol used was focused on producing monoclonal antibodies to both whole-cell and soluble microbial antigens.

The observed fusion frequency at $1 \times 10^4$ cells/well, was 27% positive for macroscopic growth after 28 days, with 3.1% being ELISA-positive to *B. gingivalis*. One percent of the wells were growth-positive at dilutions of $5 \times 10^3$ and $1 \times 10^3$ cells/well after 28 days. However, only wells with $5 \times 10^3$ cells had any ELISA-positive supernatants (2% of the wells).

EXAMPLE II

Specificity of Monoclonal Antibodies

The monoclonal antibodies to *B. gingivalis* were characterized, after cloning by both "limiting dilution" and "soft-agar" techniques. The specificity of these antibodies was studied thoroughly by ELISA using 27 formalin-fixed whole-cell antigens (14 *B. gingivalis* isolates plus 13 other oral microbial isolates, as listed in Table I, below).

The monoclonal cell-free culture supernatants were screened by the microtiter plate ELISA method described by Ebersole et al., ibid., with some modification. The whole-cell bacterial antigen preparations were diluted 1:25 in pH 9.6 carbonate-bicarbonate coating buffer (prepared by adding sufficient water to 0.2 g $NAN_3$, 1.59 g $Na_2CO_3$ and 2.93 g $NaHCO_3$ to make 1 L of solution), and a 200 µL quantity of the test sample was placed into each of the wells of 96-well polystyrene plates. The antigen-coated plates were incubated overnight at 4° C. in a moist chamber. The following morning the plates were washed three times in a PBS wash buffer containing 0.1% bovine serum albumin (BSA) and a surfactant such as polyoxyethylene sorbitan monolaurate. A blocking solution containing 1% BSA in PBS was applied to the plates and incubated at 37° C. for 1.5 hours, after which the plates were again washed three times in the wash buffer. Either normal mouse serum, immune mouse serum, fresh basal medium, or cell-free hybridoma supernatant fluid was added to the wells of the plates (100 µL), and the plates were incubated for two hours at 37° C. The plates were then washed with PBS wash buffer three times, and a 200 µL quantity of a 1:500 dilution of rabbit antimouse-IgG&IgM antibody, conjugated with alkaline phosphatase in PBS-1% BSA, was added to the wells of the assay plates. The plates were incubated for two hours at 37° C. and again washed three times with wash buffer. The substrate solution, consisting of p-nitrophenyl phosphate (5 mg/mL) in diethanolamine buffer, was then added to the plates. The plates were then incubated at room temperature until the positive controls reached an Optical Density (O.D.) of >1.5 when read at 405 nm in a Titertek Multiskan MC spectrophotometer. The results are shown in Table I.

Hybridoma BGII, VF9/2D has been deposited with the American Type Culture Collection under acession number ATCC HB 9968.

TABLE 1

ELISA Specificity Of Monoclonal Antibodies[a]

| Antigen Source | | | Antibody Source | |
|---|---|---|---|---|
| Organism | Strain | Pos. Serum | BG-II VF9/2D | BG-II VF9/3A |
| *Bacteroides gingivalis* | ATCC33277[b] | 2.60 | 1.71 | 0.70 |
| | D13B11[c] | 2.12 | 0.80 | 0.21 |
| | D40C4[c] | 1.60 | 0.43 | 0.10 |
| | D55D29A[c] | 1.65 | 0.22 | 0.16 |
| | D67D9[c] | 1.22 | 0.30 | 0.02 |
| | D82F5[c] | 1.85 | 0.12 | 0.10 |
| | D83T3[c] | 2.14 | 0.37 | 0.27 |
| | D84D2[c] | 0.89 | 0.28 | 0.02 |
| | D86B6[c] | 1.87 | 0.46 | 0.14 |
| | 381[d] | 1.60 | 1.10 | 0.30 |
| | 376[d] | 1.04 | 0.11 | 0.01 |
| | JKG-1[e] | 1.53 | 1.00 | 0.18 |
| | JKG-5[e] | 0.84 | 0.13 | 0.10 |
| | JKG-9[e] | 1.27 | 0.25 | 0.21 |
| Positive Reactions/Strains Tested = | | 14/14 | 14/14 | 11/14 |
| *B. intermedius* | MAZZA | 0.10 | 0.01 | 0.01 |
| | 7Y | 0.10 | 0.01 | 0.01 |
| | 12516[c] | 0.10 | 0.03 | 0.01 |
| | 13025[c] | 0.14 | 0.00 | 0.01 |
| | 13042[c] | 0.12 | 0.01 | 0.00 |
| | 13043[c] | 0.13 | 0.01 | 0.00 |
| *B. asaccharolyticus* | ATCC25260[b] | 0.10 | 0.01 | 0.00 |
| *B. melaninogenicus* | ATCC25845[b] | 0.17 | 0.01 | 0.00 |
| *B. maccacae* | ATCC33141[b] | 0.02 | 0.01 | 0.05 |
| *Capnocytophaga ochracea* | ATCC27872[b] | 0.11 | 0.01 | 0.01 |
| Fusobacterium sp. | | 0.17 | 0.01 | 0.01 |
| *Streptococcus mutans* | OMZ-176 | 0.07 | 0.01 | 0.01 |
| | NTCC10449 | 0.06 | 0.01 | 0.01 |
| Positive Reactions/Strains Tested = | | 10/13 | 0/13 | 0/13 |

[a]Optical Density values at 405 nm; 45-minute assay.
[b]American Type Culture Collection, Rockville, MD.
[c]Virginia Polytechnic Inst. and State U., Blacksburg, VA.
[d]Forsyth Dental Center, Boston, MA.
[e]U. of Michigan, Ann Arbor, MI.

ELISA was also performed using soluble cell extracts on most of the same isolates, with similar results. The two clone groups shown produced antibodies that were never observed to cross-react with any of the non-*B. gingivalis* microbial antigens. However, clone BGII, VI F9/3A was found to detect only some of the *B. gingivalis* isolates (11 of 14). Only the monoclonal antibodies from clone BGII, V F9/2D were able to detect antigen from all 14 *B. gingivalis* isolates. The 1:400 positive polyclonal mouse serum was also able to detect all 14 *B. gingivalis* antigens. However, this unadsorbed mouse immune serum also cross-reacted with 10 of the 13 non-*B. gingivalis* whole-cell antigens.

The procedure for characterizing the antibody subclass of each monoclonal antibody was identical except for the substitution of either rabbit antimouse IgA, IgG1, IgG2a, IgG2b, IgG3, IgM, κ chain, or λ chain specific antibodies conjugated with alkaline phosphatase. Conventional double immunodiffusion and radial immunodiffusion were also used to verify the antibody isotype ELISA results and to quantitate the specific monoclonal antibody concentrations present in the culture supernatants.

The immunoglobulin isotypes are shown in Table 2. The BGII clones, responding to whole-cell immunogens, secreted two antibody isotypes. The BGII, V F9/clones secreted only IgG2b heavy-chain antibodies with kappa light chains, while the BGII, VI F9 clones produced IgG1 heavy-chain antibodies with kappa light chains. These results were obtained by ELISA, by double immunodiffusion (Ouchterlony, in *Handbook of Immunodiffusion and Immunoelectrophoresis*, Ann Arbor Science Publishers, Ann Arbor, Mich. (1968), and by radial immunodiffusion (*Methods in Immunology*, Garvey, Cremer and Sussdorf, id., 321–327, W. A. Benjamin, Inc., 1977) against isotype-specific anitsera.

TABLE 2

Immunoglobulin Subclass Characterization

| Clone | Antibody Isotype | Light Chain |
|---|---|---|
| BCII, V F9/2D | IgG2b | kappa |
| BGII, V F9/4K | IgG2b | kappa |
| BGII, V F9/5A | IgC2b | kappa |
| BGII, VI F9/3A | IgG1 | kappa |
| BGII, VI F9/3E | IgG1 | kappa |
| BGII, VI F9/3I | Igc1 | kappa |

The sensitivity of the monoclonal antibodies to detect various concentrations (wet weights) of *B. gingivalis* ATCC 33277 formalin-fixed whole-cell antigens was compared using pooled mouse immune serum (1:400 dilution) as a positive control (Table 3). The results showed a linear pattern over the range of antigen concentrations, with a limit near 7.8 μg ($1.1 \times 10^3$ cells by direct count) for BGI, VII C2/E2 and BGII, V F9/2D supernatants, and about 31 μg ($4.6 \times 10^3$) for BGII, VI F9/3A. The unadsorbed mouse antiserum could detect less than 7.8 μg of *B. gingivalis* whole cells (fewer than $1.1 \times 10^2$ cells).

TABLE 3

Relative ELISA Sensitivity Of Monclonal Antibodies And Mouse Immune Serum For *B. Gingivalis* Antigen Concentrations

| Antigen Concentration[a] (μg/well) | Antibody Source[b] | | | |
|---|---|---|---|---|
| | Iscove's Control | Pos. Serum | BG-I VII C2/ E2 | BG-II VF9/2D | BGII, VIF9/3A |
| 1,000.0 | 0.07 | 2.18 | 1.48 | 1.33 | 0.58 |
| 500.0 | 0.05 | 1.78 | 1.06 | 0.82 | 0.47 |
| 250.0 | 0.04 | 1.72 | 0.70 | 0.70 | 0.40 |
| 125.0 | 0.03 | 1.24 | 0.67 | 0.53 | 0.25 |
| 62.5 | 0.04 | 1.20 | 0.56 | 0.42 | 0.26 |
| 31.2 | 0.01 | 0.85 | 0.46 | 0.45 | 0.13 |
| 15.6 | 0.03 | 0.82 | 0.33 | 0.32 | 0.10 |
| 7.8 | 0.03 | 0.40 | 0.19 | 0.10 | 0.04 |

[a]Wet weight of formalin fixed *B. gingivalis* ATCC 33277 whole cells.
[b]O.D. values at 405 nm.

EXAMPLE III

Determination of Antigen Utilizing Biotin-Avidin Primary-Secondary Antibody Enhanced ELISA A pH 9.6 coating buffer is prepared to contain 1.59 g $Na_2CO_3$, 2.93 g $NaHCO_3$, 0.2 g, $NaN_3$ and 1000 mL distilled water. Dilute the 25 microbial whole cell antigens listed in Table I as required with protein coating buffer consisting of 1.0 mL 50×panacoat protein coating solution to 50 mL coating buffer. Dispense 100 μL of the resulting clinical antigen sample to each well of a 96 well Immulon 2 ELISA plate. 50 μL of a coating buffer prepared by diluting 3×coating buffer 1:50 with panacoat protein coating solution is then added to each well. *Bacteroides gingivalis* 33277 is dispensed in columns 1 through 4.

After the antigen is added, incubate the plate at 2°–8° C. overnight. An optical density measurement of the plate is subsequently performed at 414 nm using a Titerek Multiskan MC spectrophotometer.

A pH 7.4 phosphate buffer solution (PBS) is prepared to contain 8.0 g NaCl, 0.2 g $KH_2PO_4$, 2.9 g $Na_2HPO_4.12 H_2O$, 0.2 g KCl, 0.2 g $NaN_3$ and 1000 mL distilled water. A 0.5% glutaraldehyde—PBS solution is prepared by adding 0.1 mL of 50% glutaraldehyde solution to 10 mL PBS. The plates are then spun for 15 minutes at 2000 rpm. After flicking the plates, 100 µL of the 0.5% glutaraldehyde—PBS solution is added to each well and the plate incubated at room temperature for 15 minutes. The plates are again flicked and washed three times with a cold PBS wash solution prepared to contain 1000 mL PBS, 1.0 g bovine serum albumin (BSA), and 0.5 ml of a surfactant such as polyoxyethylene sorbitan monolaurate. 200 µL of a blocker solution prepared to contain 20 mL PBS, 0.05 g of 0.25% BSA, and 0.15 g glycine is added to each well and the plate incubated at room temperature for 30 minutes. Wash the plate three additional times with cold PBS wash solution.

Add, to each of the wells in columns 1 and 2, 150 µL of Iscove's Modified Dulbecco's Medium (IMDM) with supplements. Then add 150 µL of monoclonal cell-free culture supernatant from hybridoma BGII, VF9/2D to all wells in columns 3 through 12. Incubate the plates for 1 hour at 37° C. in an Enzyme-linked Immunoassay (EIA) incubator, and again wash three times with cold PBS wash solution.

Biotin labelled second antibody conjugate is prepared by diluting one part biotin labelled-affinity purified Rabbit anti-mouse IgG in 5000 parts 0.1% BSA—PBS solution. Add 100 µL of this resulting solution to each well of the ELISA plate and incubate the plate for one hour at 37° C.

Next, wash the plate three times with cold PBS wash solution. Prepare an alkaline phosphatase-avidin conjugate solution to contain 0.1 mL alkaline phosphatase-avidin conjugate in 500 mL 0.1% BSA—PBS solution. Then dispense 100 µL of this conjugate solution to each of the wells. Incubate the plate for one hour at 37° C., and wash it three more times with cold PBS wash solution.

Prepare diethanolamine buffer by mixing 98 g diethanolamine, 800 mL water, 0.2 g sodium azide, and 0.1 g $MgCl_2.6H_2O$, adding sufficient 1M HCl to attain a pH of 9.8 and then adding additional water to a volume of 1 liter. Store this solution at 4° C. in the dark and allow to warm to room temperature prior to use.

Prepare an alkaline phosphatase substrate solution immediately prior to use by dissolving one 5 mg tablet of disodium p-nitrophenyl phosphate into 5 mL of the warmed 10% diethanolamine buffer. 200 µL of the alkaline phosphatase substrate solution is then added to each well of the plate which is subsequently incubated in the dark at room temperature until a yellow color develops. After each plate develops, add 50 µL of a 2N NaOH stopping solution to each well.

Measure the optical density in a Multiskan MC spectrophotometer at a wave length of 405 nm.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A monoclonal antibody produced by the hybridoma deposited under ATCC accession number HB 9968 that specifically binds to *Bacteroides gingivalis*.

2. A diagnostic reagent comprising the monoclonal antibody of claim 1 linked directly or indirectly to a detectable label.

3. A diagnostic reagent according to claim 2, wherein the detectable label is an enzyme.

4. A diagnostic reagent according to claim 2, wherein the detectable label is a fluorescent marker.

5. A diagnostic reagent according to claim 2, wherein the detectable label is a radionuclide.

6. A diagnostic reagent according to claim 2, wherein the monoclonal antibody is indirectly linked to a detectable label via a secondary antibody that specifically binds to the monoclonal antibody and wherein the secondary antibody is bound directly or indirectly to a detectable label.

7. A diagnostic reagent according to claim 6, wherein the detectable label is an enzyme.

8. A diagnostic reagent according to claim 6, wherein the detectable label is a fluorescent marker.

9. A diagnostic reagent according to claim 6, wherein the detectable label is a radionuclide.

10. A diagnostic reagent according to claim 6, wherein the secondary antibody is covalently linked to biotin and the detectable label is coupled to avidin or streptavidin.

11. A diagnostic reagent according to claim 10, wherein the detectable label is an enzyme.

12. A diagnostic reagent according to claim 10, wherein the detectable label is a fluorescent marker.

13. A diagnostic reagent according to claim 10, wherein the detectable label is a radionuclide.

14. A method for detecting *Bacteroides gingivalis* comprising the steps of:

(a) contacting a medium suspected to contain *Bacteroides gingivalis* with the monoclonal antibody of claim 1 linked directly or indirectly to a detectable label; and (b) detecting the label, whereby the presence of *Bacteriodes gingivalis* in the medium is determined.

15. A method according to claim 14, wherein the detectable label is an enzyme.

16. A method according to claim 14, wherein the detectable label is a fluorescent marker.

17. A method according to claim 14, wherein the detectable label is a radionuclide.

* * * * *